United States Patent [19]

Riggs, Jr.

[11] 4,190,501
[45] Feb. 26, 1980

[54] PROCESS FOR MEASURING INTERNAL METAL STRESS

[75] Inventor: Olen L. Riggs, Jr., Bethany, Okla.

[73] Assignee: Transworld Drilling Company, Oklahoma City, Okla.

[21] Appl. No.: 935,549

[22] Filed: Aug. 21, 1978

[51] Int. Cl.² .......................................... G01N 27/46
[52] U.S. Cl. ................................. 204/1 T; 204/195 R; 204/195 F
[58] Field of Search ............... 204/1 T, 195 R, 195 F

[56] References Cited

U.S. PATENT DOCUMENTS

| | | | |
|---|---|---|---|
| 2,183,531 | 12/1939 | Allison | 204/195 R |
| 2,531,747 | 11/1950 | Stearn | 204/195 R |
| 2,894,882 | 7/1959 | Strodtz | 204/1 T |
| 2,960,455 | 11/1960 | Frankenthal | 204/195 R |
| 3,492,860 | 2/1970 | Bailey | 204/195 C |
| 3,627,664 | 12/1971 | Grimaldi et al. | 204/195 R |
| 3,705,089 | 12/1972 | Grubb | 204/195 F |
| 3,808,105 | 4/1974 | Rozeanu | 204/195 R |
| 3,871,985 | 3/1975 | Crippen et al. | 204/195 R |
| 3,975,681 | 8/1976 | Angelini et al. | 204/195 R |
| 4,006,063 | 2/1977 | Ensanian | 204/195 R |

*Primary Examiner*—T. Tung
*Attorney, Agent, or Firm*—William G. Addison

[57] ABSTRACT

An apparatus and procedure for measuring internal metal stress and determining the effectiveness of metal stress-relief treatments. More specifically, an apparatus and procedure for determining the effectiveness of metal stress-relief by heat treatment in the heat-affected zone surrounding a metal weld. The apparatus comprises an electrical half-cell and a unique bridge system designed to provide intimate physical contact between the electrical half-cell and a metal surface. The apparatus permits a metal to half-cell electrical potential measurement to be made at various locations upon the metal surface. The electrical potential measurements provide a means of evaluating the efficiency of a stress-relief treatment in reducing internal stress within a metal.

5 Claims, 4 Drawing Figures

PROCESS FOR MEASURING INTERNAL METAL STRESS

BACKGROUND OF THE INVENTION

1. Field of the Invention

An apparatus and process for determining the effectiveness of metal stress-relief treatment.

2. Description of the Prior Art

Generally, when metals are shaped by bending or when metals are connected together by means such as welding, areas of high internal stress are created within the metal. If the stress is not relieved by, for example, heat treatment under controlled conditions or the like the metal is subject to severe corrosion in the area of high stress when placed in a conducting medium.

Metallic corrosion normally proceeds from areas of a metal which are more anodic than the surrounding areas of the metal to those areas that are less anodic. A concentration of internal stress within an area of a metal causes that area to be more anodic than the surrounding area. For example, when the end of a steel pipe is welded to a steel flange, high internal stresses are produced in the area of the weld (the heat-affected zone). Unless the steel pipe and flange thereafter are properly heat treated under controlled conditions, the steel pipe and flange will undergo severe corrosion at the heat-affected zone when the pipe is placed in a conducting medium. Such corrosion eventually will cause premature failure of the pipe.

The problem in reducing the effects of high internal stress in metals is monitoring or detection of the high stress area following a stress-relief treatment, such as heat treatment. This inventor knows of no prior art device which solves this problem short of metalurgical analysis involving complicated destructive sampling procedures.

SUMMARY OF THE INVENTION

The discovery now has been made that the apparatus and process hereinafter set forth provide a simple, rapid and efficient means for determining the effectiveness of metal stress-relief treatments.

The apparatus comprises an electrical half-cell and a unique bridge system designed to provide intimate physical contact between the electrical half-cell and the surface of a metal. The half-cell is connected to a monitoring means capable of displaying and/or recording the electrical potential measured between the half-cell and the metal's surface upon contacting the metal with the bridge at discrete locations. The electrical potential data provide a means of determining the presence of localized high internal metal stress and the magnitude of that stress in relation to that of the surrounding metal. The data is evaluated by graphical analysis or other suitable means which effects a comparison between individual datum. Deviation in the data indicates the presence of internal stress. The magnitude of the deviation can be correlated to the severity of metallic corrosion which will result upon placing the metal in an electrically conductive medium.

DESCRIPTION OF THE PREFERRED EMBODIMENT

Figure 1:
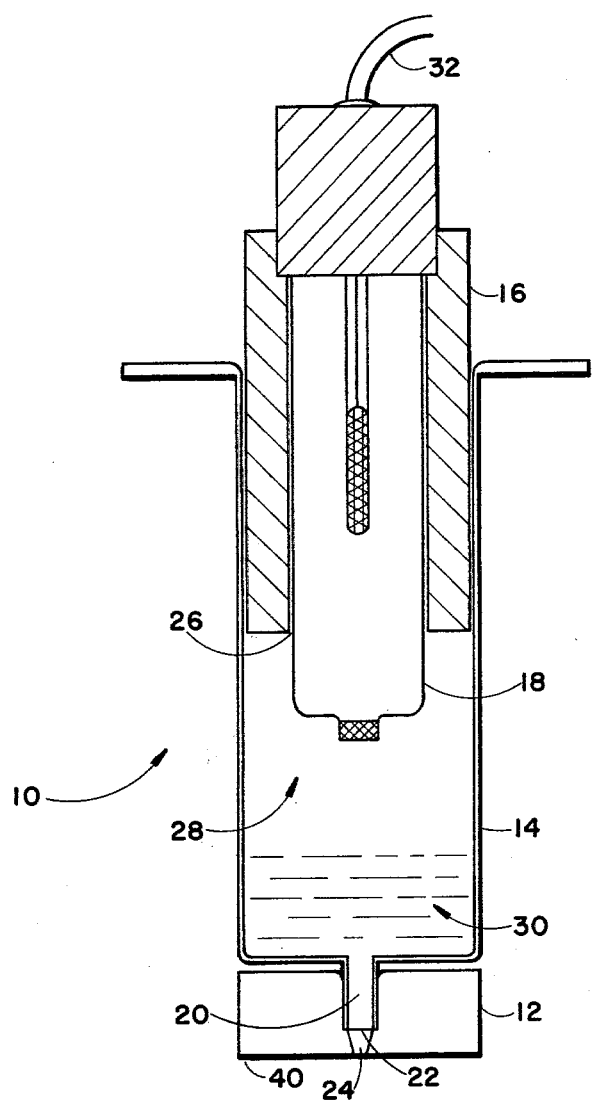
FIG. 1 is a schematic illustration of a half-cell assembly of this invention.

Turning now to FIG. 1, a half-cell assembly 10 is illustrated. The half-cell assembly 10 comprises a compressible mask 12, a body 14 having a passageway 28 therethrough, a wiping collar 16 and a reference electrode half-cell 18 having an electrical lead 32.

The body 14 may comprise any material which is sufficiently rigid to support the reference half-cell 18 contained therein and which is substantially electrically inert. For example, body 14 can comprise glass or various plastic-type materials such as polypropylene, polyethylene, polyvinyl chloride and the like. The body 14 has one end 20 of preferably reduced cross-sectional area having an opening 22 comprising one end of passageway 28. The end 20 of body 14 is inserted into a passageway 24, contained in compressible mask 12, which has a cross-sectional area less than that of end 20 of body 14 and is engaged therein in communicating alignment by compressional force. The compressible mask 12 can comprise any material that is suitably flexible and compressible, such as rubber and the like. The passageway 24 provides communication between the metal surface to be tested and the opening 22 in body 14.

The reference electrode half-cell 18 is inserted into a passageway 26 in wiping collar 16 to extend therethrough and preferably is frictionally engaged therein. The engagement means between passageway 26 and reference electrode half-cell 18 also can comprise any other mounting method which results in securing the reference electrode half-cell 18 within the passageway 26. The wiping collar 16 can comprise any material that is suitably flexible and compressible, such as rubber and the like.

The reference electrode half-cell 18 can comprise any one of the commercially available reference electrodes or it may comprise a specially prepared reference electrode. Examples of suitable reference electrodes are calomel electrodes, mercury/mercury chloride electrodes, mercury/mercury sulfate electrodes and the like.

The wiping collar 16 and reference electrode half-cell 18 then are inserted into passageway 28 through the opening in the end opposite end 20 of body 14. The wiping collar 16 is of sufficient cross-sectional area that upon insertion into passageway 28 it is slideably engaged therein by friction or by other suitable engagement means between the surface of passageway 28 in body 14 and the outer surface of wiping collar 16.

Prior to insertion of the wiping collar 16 and reference electrode half-cell 18 into passageway 28 in body 14, an electrolyte solution 30 is prepared. The solution 30 is prepared by dissolving a sufficient quantity of a mineral salt compatable with the particular reference electrode half-cell 18 in distilled water to form a saturated solution. A gelling agent, such as agar or the like, can be added to the electrolyte solution 30 in sufficient quantity to thicken the solution into a gelatinate. A quantity of the saturated electrolyte solution 30 then is inserted into passageway 28. Upon insertion of wiping collar 16 and reference electrode half-cell 18 into passageway 28 the electrolyte solution 30 is contacted and compressed thereby. The application of axial force to the wiping collar 16 causes the electrolyte solution 30 in contact therewith, to be extruded through opening 22 in body 14 and through passageway 24 in compressible mask 12.

Alternatively, the electrolyte solution 30 may be introduced into passageway 28 after insertion of wiping collar 16 and reference electrode half-cell 18 into passageway 28.

Figure 2:
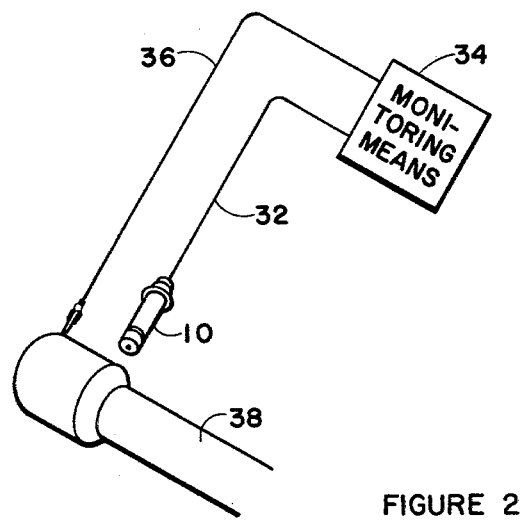
FIG. 2 is a schematic illustration of the process and apparatus of this invention.

Referring now to FIG. 2, the electrical lead 32 of reference electrode half-cell 18 is connected to a electrical potential monitoring means 34. The monitoring means can comprise any device which is capable of displaying and/or recording the electrical potential measured between the metal and the half-cell 18 upon completion of the electrical circuit.

An electrical lead 36 is connected by any suitable means from the monitoring means 34 to a metal 38, the surface of which is to be tested for internal stress. If any foreign matter or corrosion products are present on the metal surface to be tested, it is necessary to clean the surface. The cleaning can be accomplished by any means which provides a fresh metal surface for testing.

To perform a test, the half-cell assembly 10 is brought into electrical contact with the surface of metal 38 by a unique bridge means designed to provide intimate physical contact between the electrical half-cell and the metal's surface.

The bridge system comprises the passageway 28 of body 14, the compressible mask 12 and passageway 24 therein and the saturated electrolyte solution 30 (FIG. 1). The contact is created by first applying sufficient axial force to the wiping collar 16 to compress the electrolyte solution 30 in contact therewith and cause said solution to be extruded in a continuous manner through passageway 24 in compressible mask 12. Excess extruded electrolyte solution 30 then is removed to provide an electrolyte surface across the diameter of passageway 24 substantially adjacent to a surface 40 of compressible mask 12. The surface 40 of compressible mask 12, then is positioned against the surface of metal 38 which is to be tested. Axial force then is applied to the mask 12 to compress mask 12 against the surface of metal 38 to provide substantial contact between the surface of metal 38 and electrolyte solution 30. The contacting of electrolyte 30 with the surface of metal 38 completes an electrical circuit and enables an electrical potential measurement to be made with monitoring means 34 between the reference electrode half-cell 18 and metal 38. The axial force applied to compressible mask 12 then is removed. To eliminate the possibility of contamination of the bridging means after a test, sufficient additional axial force then is applied to wiping collar 16 to extrude additional electrolyte solution 30 through passageway 24. The excess electrolyte solution 30 is removed and the surface 40 of compressible mask 12 then is positioned against a new test location on the surface of metal 38.

To develop a suitable profile from which the presence and magnitude of localized high internal stress can be evaluated, a series of tests are conducted in a line generally perpendicular to the line of suspected high stress caused by bending a piece of metal or by joining two or more pieces of metal. The result of such a series of tests on a sample of carbon steel drill pipe is graphically illustrated in FIG. 3. The sample included a pipe flange, a weld with a surrounding heat-affected zone and a section of unaffected pipe. A test was conducted on the flange, in the heat-affected zone near the weld and at a point beyond the heat-affected zone near the weld and at a point beyond the heat-affected zone on the pipe. The reference electrode half-cell 18 in half-cell assembly 10 was a standard calomel electrode and the electrolyte solution 30 was a saturated potassium chloride solution. The sharp deviation in the profile illustrated in FIG. 3 indicates that high localized internal stresses exist near the weld in the heat-affected zone of the pipe.

After a preliminary determination of the presence of high internal stress areas, the metal is subjected to any suitable stress-relief treatment. The normal method for stress-relief of a metal is through heat treatment under controlled conditions. After the stress-relief treatment, the metal again is tested to develop a new stress profile. The profile of a metal which has received satisfactory stress-relief treatment is graphically illustrated in FIG. 4.

In this instance, the sample of carbon steel drill pipe was subjected to a stress-relief treatment which comprised heating the sample in a furnace to a temperature of 1175 degrees F. and maintaining the sample at that temperature for 15 minutes. The sample then was removed from the furnace and immediately cooled by quenching. Tests then were performed using the same half-cell assembly 10.

Figures 3, 4:
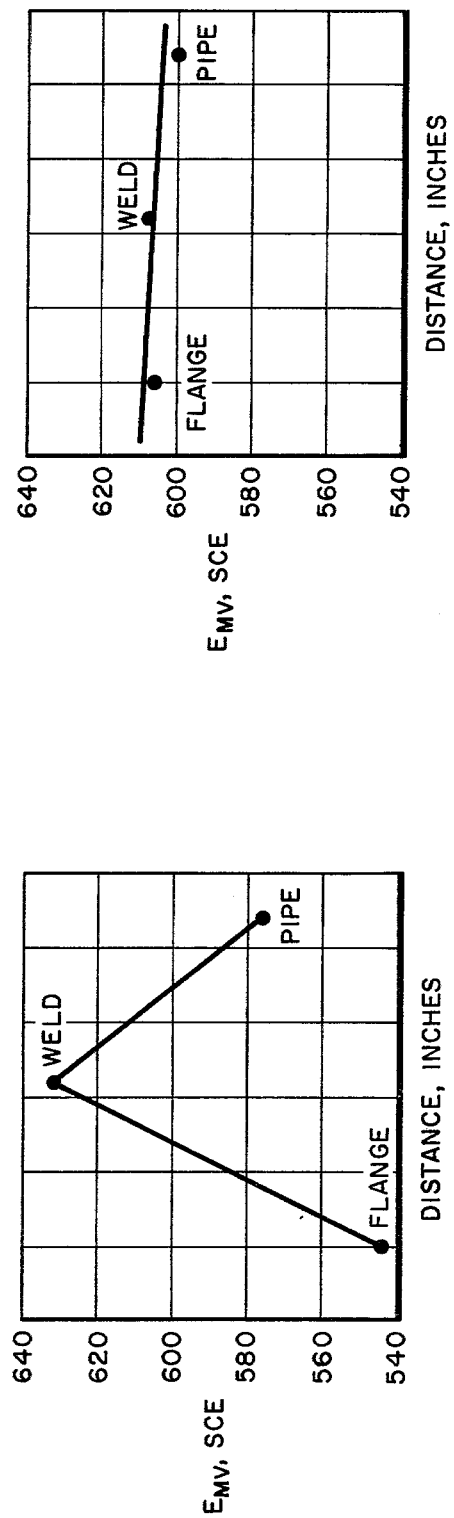
FIG. 3 is a graphical illustration of recorded metal to half-cell electrical potential measurements for a metal sample containing a heat-affected zone produced by welding.
FIG. 4 is a graphical illustration of recorded metal to half-cell electrical potential measurements for a metal sample containing a heat-affected zone after stress-relief treatment.

The profile illustrated in FIG. 4 clearly shows only a small deviation in the electrical potential measurements of the metal surface across the area of former high internal stress as compared to the substantial deviations present in the profile of the untreated metal surface illustrated in FIG. 3. Therefore, the stress-relief treatment was effective and the probability of severe corrosion causing premature metal failure is substantially reduced.

Alternatively, tests can be conducted on a metal only after stress-relief treatment. The effectiveness of the stress relief treatment then is determined by the deviation in the slope of the profile illustrated in FIG. 4.

In this instance, effective stress-relief treatment is achieved when the slope of the plotted line only has a small random deviation from zero slope (as illustrated in FIG. 4).

The device of this invention is particularly suitable for testing metals such as pipe while located at field storage facilities. A single individual can carry and operate the equipment and a series of tests on a particular metal sample normally is conducted in less than five minutes. This provides a simple, rapid and efficient means for determining the effectiveness of stress-relief treatment. The testing can be conducted on each piece of pipe in a pipe storage rack, or random sampling may be employed for evaluation of large numbers of pipes.

While the present invention has been described in what at present is considered to be the preferred embodiment thereof, it is to be understood that changes or modifications in the apparatus and procedure of this invention can be made without departing from the spirit or scope of the invention as defined by the following claims.

What is claimed is:

1. A process for measuring internal stress in metals by surface testing comprising:
   providing a metal surface;

providing a half-cell assembly comprising a body having a passageway therethrough with a compressible mask having a passageway therethrough positionally disposed and mounted upon one end of the body surrounding the passageway therethrough and in communicating alignment therewith, a reference electrode half-cell with a wiping collar having a passageway therethrough positionally disposed and mounted about the reference electrode half-cell, the wiping collar being at least partially inserted within the open end of the passageway through the body opposite the end whereon the compressible mask is positioned, and a saturated electrolyte solution contained in the passageway within the body;

positioning the passageway through the compressible mask of the half-cell assembly in juxtaposition with the metal surface;

compressing the compressible mask against the metal surface by application of axial force; and measuring the electrical potential between the metal surface and the reference electrode half-cell.

2. The process of claim 1 defined further to include the step of:

applying axial force to the wiping collar within the half-cell assembly to compress the saturated electrolyte solution contained therein and cause the solution to be extruded through the passageway in the compressible mask.

3. The process of claim 1 defined further to include the steps of:

removing the axial force causing compression of the compressible mask;

applying axial force to the wiping collar within the half-cell to compress the saturated electrolyte solution contained therein and cause the solution to be extruded through the passageway in the compressible mask;

removing the extruded electrolyte solution;

repositioning the passageway through the compressible mask of the half-cell assembly in juxtaposition with a new portion of the metal surface;

recompressing the compressible mask against the metal surface by application of axial force; and measuring the electrical potential between the new portion of the metal surface and the reference electrode half-cell.

4. The process of claim 1 in which the saturated electrolyte solution is defined further as including a gelling agent to thicken the solution into a gelatinate.

5. The process of claim 4 in which the gelling agent is agar.

* * * * *